United States Patent [19]
Fischer et al.

[11] Patent Number: 5,687,718
[45] Date of Patent: Nov. 18, 1997

[54] DEVICE FOR CONTINUOUSLY DETECTING BLOOD PARAMETERS

[75] Inventors: Bernhard Fischer, Leonberg; Martin Zoll, Gechingen; Joachim Wender, Leonberg; Frank Rochlitzer, Altdorf, all of Germany

[73] Assignee: Hewlett-Packard Company, Palo Alto, Calif.

[21] Appl. No.: 490,320

[22] Filed: Jun. 14, 1995

[30] Foreign Application Priority Data

Jul. 9, 1994 [DE] Germany .................. 44 24 267.0

[51] Int. Cl.$^6$ .................................................. A61B 5/00
[52] U.S. Cl. .................................................. 128/632
[58] Field of Search .................................. 128/632, 634, 128/635, 637, 672, 673, 692; 604/44; 600/16

[56] References Cited

U.S. PATENT DOCUMENTS

| | | | |
|---|---|---|---|
| 3,498,289 | 3/1970 | Watanabe et al. | 128/632 |
| 4,444,498 | 4/1984 | Heinemann | 128/633 |
| 4,484,135 | 11/1984 | Ishihara et al. | 128/632 |
| 4,600,495 | 7/1986 | Fogt | 128/635 |
| 4,745,279 | 5/1988 | Karkar et al. | 128/40 |
| 4,813,423 | 3/1989 | Miyasaka . | |
| 4,841,974 | 6/1989 | Gumbrecht . | |
| 5,058,587 | 10/1991 | Kohno et al. | 128/633 |
| 5,195,963 | 3/1993 | Yafuso . | |
| 5,456,253 | 10/1995 | Steuer et al. | 128/637 |

FOREIGN PATENT DOCUMENTS

| | | |
|---|---|---|
| 0069247 | 10/1985 | European Pat. Off. . |
| 0276977 | 8/1988 | European Pat. Off. . |

*Primary Examiner*—Jennifer Bahr
*Assistant Examiner*—Eric F. Winakur

[57] ABSTRACT

Disclosed is a device for continuing detecting blood parameters. The device includes a catheter adapted to be introduced into the artery of a patient. A sensor is arranged in the catheter. A tube us adapted to be coupled to a vein of a patient and is also connected to the first catheter. A device controllably maintains blood flow across the sensor, the device being controlled such that initially the flow of blood to the first catheter via the tube is prevented so long as the detective blood parameters indicated a sufficient amount of fresh arterial blood is flowing around the sensor. In the event that a detective blood parameters indicate that an insufficient amount of blood flows around the sensor, then blood flow through the first catheter to the vein of the patient via the tube is then established.

26 Claims, 5 Drawing Sheets

DEVICE FOR CONTINUOUSLY DETECTING BLOOD PARAMETERS

FIELD OF THE INVENTION

The present invention deals quite generally with a device for continuously detecting blood parameters. More specifically, the present invention deals with a device for continuously measuring the blood gas and/or the pH value for arterial blood by means of a sensor which is attached to a catheter and which is introduced into an artery of the patient for the purpose of measurement.

DESCRIPTION OF THE PRIOR ART

A conventional type of blood gas analysis comprises the steps of taking a sample from the patient's artery by means of a syringe or a glass capillary, whereupon this blood sample is stored on ice until it has been prepared for the analysis. Although satisfactorily accurate analysis values are obtained by means of this conventional blood gas analysis, this course of action is not suitable for a continuous real time detection of blood parameters, such as blood gas values or the pH value of the arterial blood flow.

Hence, systems for the detection of blood parameters permitting a continuous almost real time detection of blood gas parameters or of the pH value of the blood have been used for some time. Such systems typically comprise a catheter which is introduced in a patient's artery. In the area of the free end of the catheter, a sensor is provided, which is used for detecting the blood gas parameter or the pH value of interest. The connection cable of the sensor extends through the catheter, passes through a sealing member and extends up to a monitor. Although good measurement accuracies can be achieved by means of such systems when a large amount of blood flows through the artery, measuring errors occur, as will be explained in detail hereinbelow, in situations where a small amount of blood or even no blood at all flows in the artery, the detected blood gas parameters or the detected pH value of the arterial blood being grossly mutilated by said measuring errors.

Such situations in which the flow of blood in the artery is substantially reduced or even brought to a complete standstill can be a direct consequence of the introduction of the free end of the catheter in the artery. Furthermore, such situations may occur when the patient's blood is cooled down, e.g. for carrying out a cardiovascular surgical operation during which the patient is connected to a heart-lung apparatus. A further reason for a substantial reduction of the blood flow in the artery can be a coagulation of blood within the artery. A blood gas sensor which is introduced in the artery and which causes an essentially reduced blood flow will not detect the expected blood gas values which would be detected in the case of fresh arterial blood, since the measured values will differ in a characteristic way from the values of the fresh arterial blood. These deviations are caused by the physiological circumstance that stagnant blood consumes oxygen itself, whereby a local increase in the carbon dioxide will be caused, and this, in turn, will have the effect that the pH value of the blood decreases. Furthermore, a diffusion of gases through arterial walls and through the skin will result in an equilibrium with the ambient air, and this, too, will have the effect that the gas concentrations in the stagnant blood will be changed in comparison with gas concentrations in flowing fresh arterial blood. In addition, it may happen that, in the case of an impaired arterial blood flow, the normally used saline solution, which is used as a rinsing solution and which flows into the artery through the arterial catheter, accumulates in front of the catheter opening instead of flowing off behind the catheter opening when seen in the direction of flow. The partial pressure of oxygen and the partial pressure of carbon dioxide of the saline solution correspond essentially to those of the ambient air. It follows that the blood gas values and the pH value, which are measured in stagnant blood by means of the known device, or these values of the rinsing solution or of a mixture of the rinsing solution and of the blood, will substantially deviate from the values of the fresh arterial blood.

U.S. Pat. No. 4,813,423 describes an instrument for measuring living body components, which includes a catheter having an interior sensor. By means of a mechanism, blood is periodically sucked into the catheter and then discharged again into the blood vessel. An alternating flow of blood, which provides good measuring conditions, is generated at the tip of the probe. An anticoagulant prevents blood clotting.

EP 0 069 247 B1 discloses a dialysis means provided with a pump.

EP 0 276 977 A2 discloses a system for measuring blood parameters in the case of which an oscillating flow of blood is caused in the area of a sensor.

U.S. Pat. No. 5,195,963 describes a system used for detecting blood constituents of the living body and including a sensor which projects beyond a distal opening.

SUMMARY OF THE INVENTION

It is an object of the present invention to provide a device for continuously detecting blood parameters which permits an increased measuring accuracy.

This object is achieved by a device for continuously detecting blood parameters, which has the following features:

a first catheter adapted to be introduced with its free end into an artery of a patient;

a sensor arranged on said catheter;

an additional catheter adapted to have its free end introduced in the patient's vein and connected to said first catheter; and a device for controllably maintaining a bloodstream from the artery via said sensor into the vein.

In accordance with an essential aspect of the present invention, a flow of blood from the artery through the catheter is enforced, said artery having inserted therein the catheter and being, for example, the radial artery. One solution is to be seen in the provision of an arterio-venous shunt for enforcing a flow of blood through the catheter. It is also possible to use an arbitrary type of pump for causing an enforced flow of blood from the blood vessel through the catheter and e.g. back to a vein. In any case, a (selectively activatable) flow of blood through the catheter, at the free end of which the sensor is located in the patient's blood vessel, is enforced in accordance with the teaching of the present invention so that the blood flowing along the sensor will inevitably have the properties of fresh arterial blood. On the basis of the teaching of the present invention, it is not only possible to arrange the sensor, relative to the end of the catheter, outside of the catheter or behind the catheter at an arbitrary point of an arteriovenous shunt a short distance in front of the opening of the catheter, as has been done in connection with the known invasive systems described, but it is also possible to dispose the sensor at a retracted position relative to the opening of the catheter and to arrange it in the interior of the catheter, since, due to the enforced flow of blood, the sensor will always be in contact with fresh arterial blood during the measurement process even if it is arranged in the above-mentioned way.

In accordance with one aspect of the present invention, the device for controllably maintaining a bloodstream from the artery via said sensor into the vein has a first branching member, the first arm of which extends to the catheter, through the second arm of which a sensor cable connected to the sensor extends, and the third arm of which is connected to a rinsing device used for supplying a rinsing solution; and a second branching member, the first arm of which extends to said first branching member, through the second arm of which the sensor cable extends to a monitor for blood parameter values, and the third arm of which serves to drain blood from the blood vessel.

In accordance with another aspect of the present invention, the first catheter is adapted to have its free end introduced into an artery of a patient and is formed as a double-lumen catheter comprising two lumina; wherein the sensor is arranged at one lumen of said double-lumen catheter.

In accordance with still another aspect of the present invention, a first lumen of said double-lumen catheter is connected to a pressure transducer and a device for supplying a rinsing solution; the sensor cable, which is connected to the sensor, extends through a second lumen of said double-lumen catheter; and the device further comprises a branching member comprising a first arm which extends to the second lumen of the double-lumen catheter, a second arm through which the sensor cable extends to a monitor for blood parameter values, and a third arm which serves to drain blood from the artery.

In a preferred embodiment of the invention, the device comprises a pump connected to the device for controllably maintaining a bloodstream and used for pumping off blood through the catheter.

In another preferred embodiment of the invention, the pump is, on the one hand, connected to the third arm of the second branching member and, on the other hand, adapted to be connected to an additional catheter communicating with a vein.

In a preferred embodiment of the invention, the device comprises a third branching member, the first arm of which extends to the second arm of the second branching member, the second arm of which leads the sensor cable in the direction of the monitor for the blood parameter values, and the third arm of which is connected to the rinsing device for the rinsing solution.

In another preferred embodiment of the invention, the pump consists of a hose-roller pump or a manually operated liquid slide valve.

In another preferred embodiment of the invention, parts of the device for controllably maintaining a bloodstream or the whole device is coated with an antithrombotic coating, e.g. heparin.

In another preferred embodiment of the invention, the device for controllably maintaining a bloodstream from the artery via said sensor into the vein has Luer-lock connection ends and wherein these Luer-lock connection ends are provided with special transition adapters, which, when connected to a Luer-lock connection, will fill the enlarged lumen located in the area of the Luer-lock connection in such a way that, in the connected condition, a homogeneous free interior lumen will be obtained in the connection area of the Luer-lock connection, said interior lumen having a free cross-section which is reduced to the interior diameter of the shunt connection.

BRIEF DESCRIPTION OF THE DRAWINGS

In the following, a preferred embodiment of the present invention will be explained in detail making reference to the drawings enclosed, in which.

DESCRIPTION OF THE PREFERRED
EMBODIMENTS OF THE INVENTION

A catheter K is introduced with its free end FE into a radial artery RA of a patient to be examined. A sensor tip ST of a sensor S extends beyond the free end FE of the catheter K, said sensor S having connected thereto a sensor cable SK. The sensor cable extends in the interior of the catheter K. The system according to the present invention comprises, as will be explained in detail hereinbelow, a device for controllably maintaining a bloodstream for controllably draining blood from the artery RA which has the catheter K inserted therein.

In the preferred embodiment shown in the present connection, the device for controllably maintaining a bloodstream comprises a first branching member Y1 whose first arm extends to the catheter K, whose second arm guides the sensor cable SK, and whose third arm is connected via a pressure transducer PT to a rinsing device (not shown) used for supplying a saline solution rinsing fluid. The second arm of the first branching member Y1 is connected to a first arm of a second branching member Y2 whose second arm serves to lead the sensor cable SK to a third branching member Y3 and whose third arm is connected via a pump P to a line, which, in turn, leads back into the vein of the patient. The second arm of the third branching member Y3 is provided with a feed-through seal F through which the sensor cable SK is guided to a blood parameter monitor (not shown). The third arm of the third branching member Y3 is connected to the rinsing device (not shown) which has already been mentioned and which is used for supplying the saline solution rinsing fluid.

Figure 1:
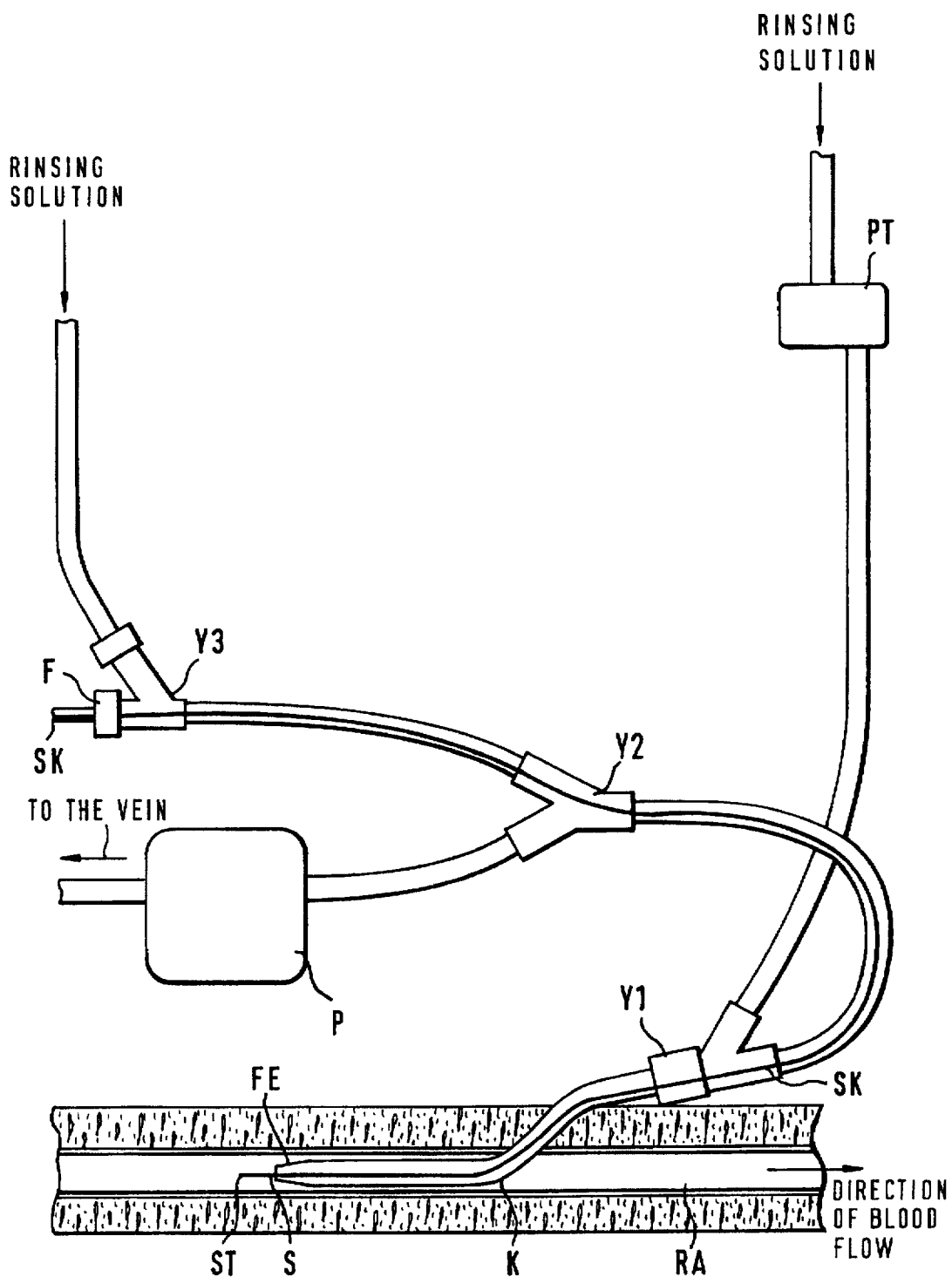
FIG. 1 shows a schematic diagram of a first embodiment of the device for continuously detecting blood parameters according to the present invention.
Figure 2:
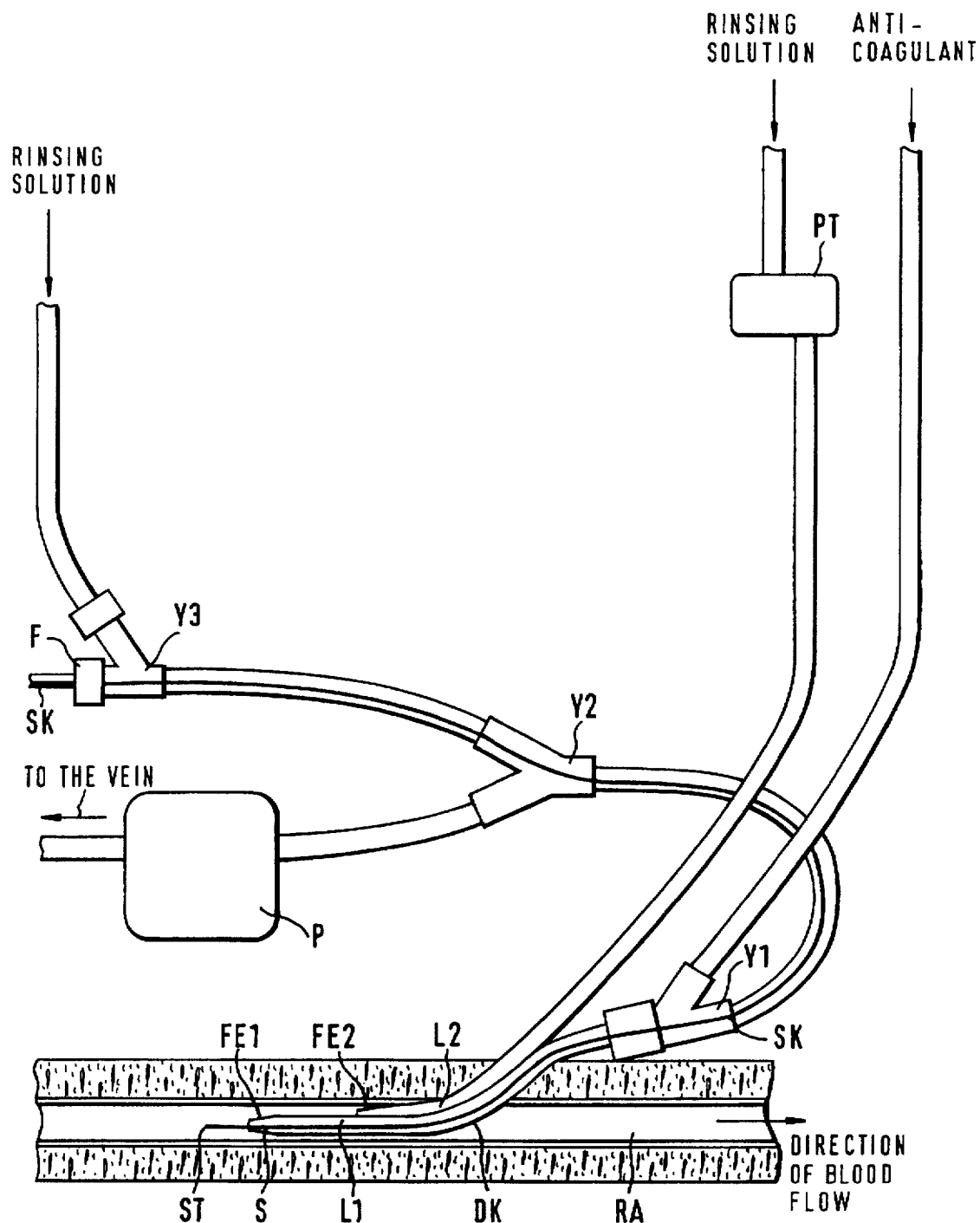
FIG. 2 shows a schematic diagram of a second embodiment of the device for continuously detecting blood parameters according to the present invention.

A second preferred embodiment, which is shown in FIG. 2 and which corresponds to the embodiment according to FIG. 1 with the exception of the deviations explained hereinbelow, comprises a double-lumen catheter DK instead of a plain catheter K. Through a lumen L1 of the double-lumen catheter, preferably through the lumen whose exit is located at the free distal end FE1 of the catheter, a sensor tip ST of a sensor S having connected thereto a connection cable is introduced into the radial artery of a patient, just as in connection with the embodiment of the plain catheter K. The second lumen L2, preferably the lumen whose exit is located at the side of the catheter body, is connected via a pressure transducer PT to a rinsing device.

In comparison with the plain-catheter embodiment, this embodiment shows the advantage that due to the fact that the invasive blood pressure measurement and the blood parameter measurement are decoupled from one another along the whole length back into the artery, the two applications are largely prevented from mutually influencing each other.

In cases in which the blood flow in the artery is supported by the pump P, the negative pressure generated by said pump P in the arterio-venous shunt will not have a pressure-reducing effect with regard to the arterial pressure applied to the pressure transducer on the side of the artery; such a pressure-reducing effect might result in reduced absolute values of the arterial blood pressure values derived. Furthermore, the pressure oscillations and pulsations which are caused during operation by the pump P, depending on the technical structural design thereof, and which propagate through the arteriovenous shunt will be kept away from the pressure transducer to a very large extent; in the present case, such pressure oscillations and pulsations may cause strong noise in and interference with the pressure signal received.

Figure 3:
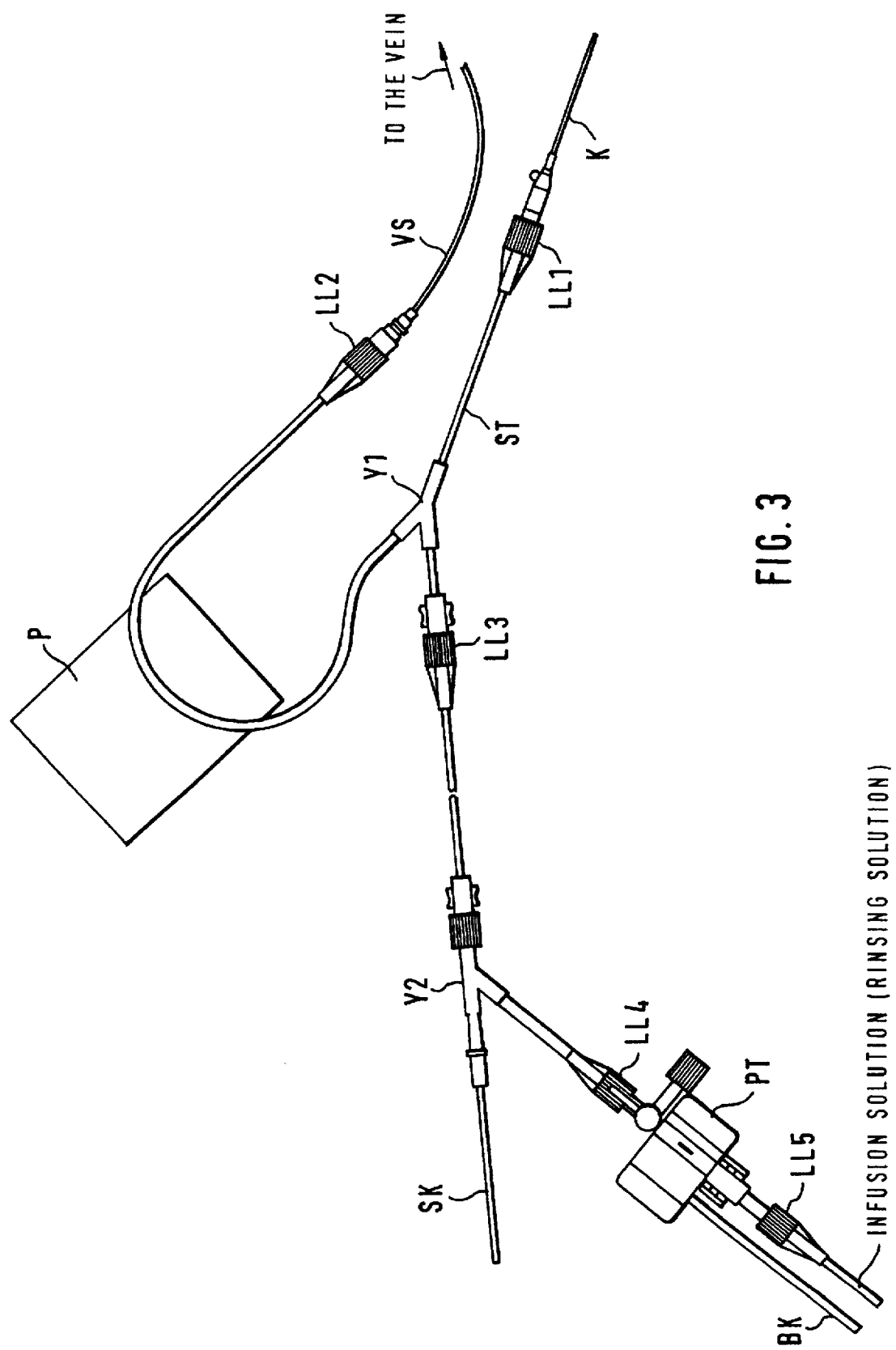
FIG. 3 shows a schematic diagram of a hose system.

FIG. 3 shows an implementation of the device for continuous detection of blood parameters according to the present invention by means of a system of hoses provided with Luer connectors. With the exception of the deviations described hereinbelow, this third embodiment corresponds to the embodiments according to FIG. 1 and 2 so that only the parts and components which are different will be explained. The pressure transducer PT has supplied thereto the infusion solution or rinsing solution. Furthermore, a blood pressure cable BK is connected to said pressure transducer PT. The pressure transducer PT communicates with the second branching member Y2, which has connected thereto the sensor cable SK. This sensor cable SK communicates via Luer-lock connections with the first branching member Y1, which has connected thereto a hose VS extending to the vein and passing through a hose pump P. The free end of the first branching member Y1 communicates with the catheter K via an additional Luer-lock connector. The Luer-lock connectors used in this system of hoses are designated by reference numerals LL1 to LL5. It is specially emphasized that, in this third embodiment according to FIG. 3, the sensor tip ST is arranged between the first branching member Y1 and the Luer-lock connector LL1 which is associated with the catheter K.

Figure 4:
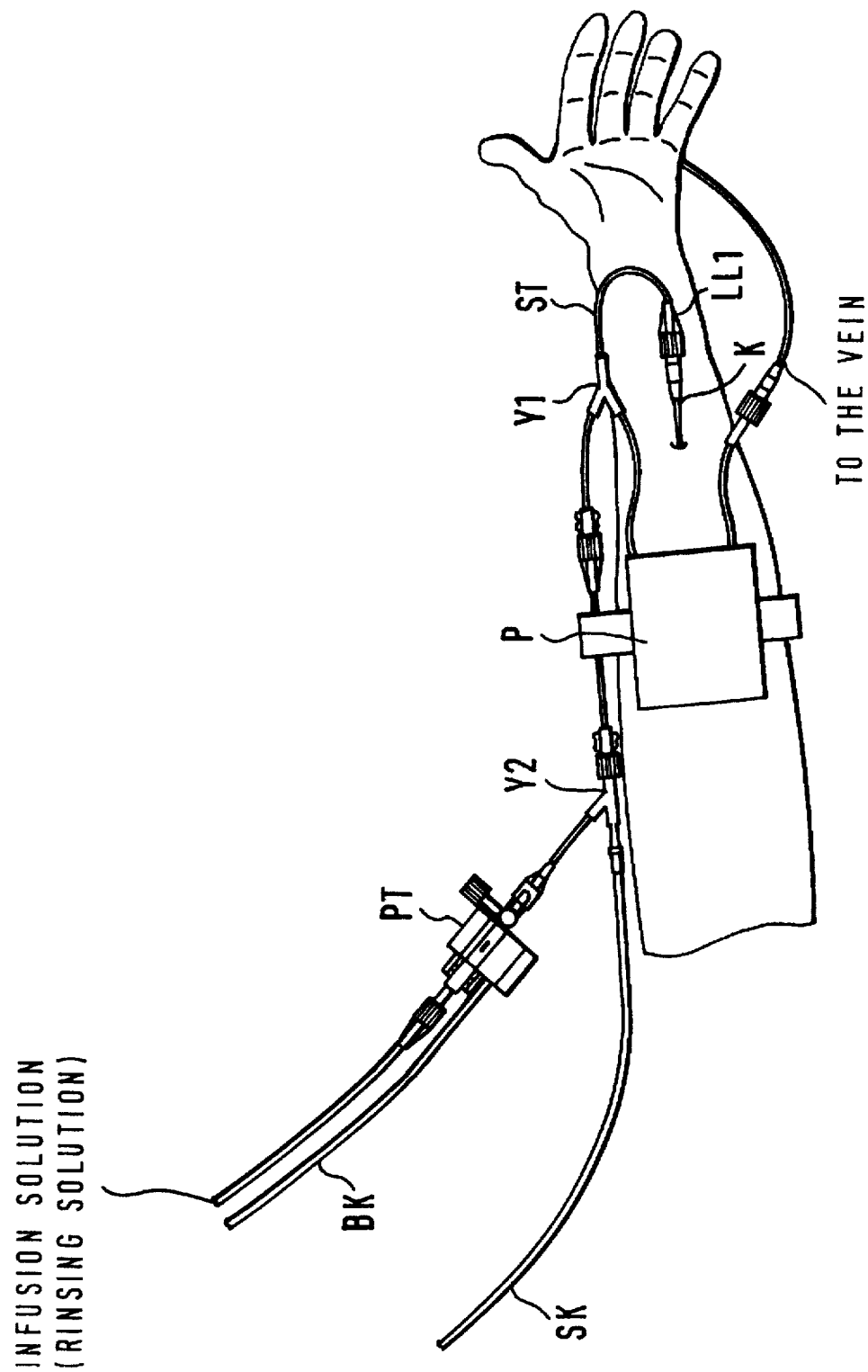
FIG. 4 shows a schematic diagram of an arteriovenous shunt.

FIG. 4 shows how the system of hoses, which is shown in FIG. 3 and which has been described making reference to said FIG. 3, is attached to the left arm of a patient for the purpose of blood parameter determination.

Figure 5:
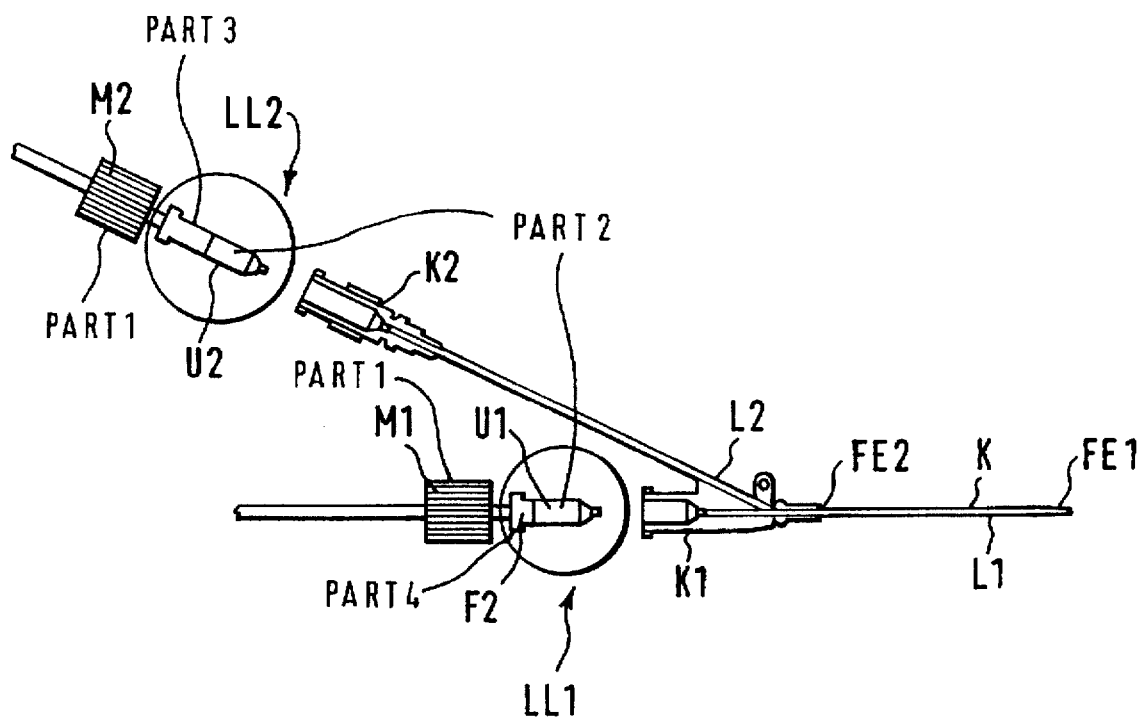
FIG. 5 shows a representation of the Luer-lock components used in connection with a double-lumen catheter.

FIG. 5 shows an even more detailed representation of Luer-lock connections used for realizing the embodiment according to FIG. 2. The catheter K has again a front exit end FE1 of the first lumen L1 as well as a rearwardly displaced second exit end FE2 of the second lumen L2, which are formed in a head portion K1 of the first Luer-lock connector LL1. A base portion F2 of the Luer-lock connector is provided with a sleeve nut M1 for engagement with the head portion K1 as well as with a transition portion U1. The transition portion U1 clampingly fits into an adequate recess of the head portion K1 in a manner which is known in connection with Luer-lock connectors. Also the additional Luer-lock connector, which is shown in FIG. 5, comprises a nut M2, a transition portion U2 and a head portion K2, which is in fluid connection with the second lumen.

In accordance with a preferred concept of the present invention, the device is operated in a three-step measurement method. In an initial measurement situation, the pump P is switched off so as to prevent any flow of blood through the catheter K. As long as it can be concluded from the measured values detected in this measurement situation that a sufficient amount of fresh arterial blood flows around the sensor S, it is not necessary to cause any artificial, enforced flow of blood around the sensor by means of an enforced blood flow through the catheter.

As soon as the measurement results suggest a situation in which a small amount of blood flows around the sensor, a simple connection to a vein of the patient, i.e. to the venous side of the blood circulation system, is established e.g. via the third arm of the third branching member without actuating the pump P. Also such a simple connection is, within the meaning of the terminology used in the patent claims, a device for controllably maintaining a bloodstream from the artery RA via the sensor S into the vein. Such an arteriovenous shunt is referred to as "Scribner shunt" in medical literature. This mode of operation permits only little control of the amount of blood flow, but in most cases of use it may suffice.

If the shunt mode of operation, which has just been described and in which the pump is not used, does not result in the desired measurement success either, the pump P will be actuated so as to force the blood to flow through the catheter along the arteriovenous shunt defined by the pump branch.

In the second- and third-mentioned modes of operation (in which blood flows through the catheter K), the sensor S may be retracted into the interior of the catheter relative to the free tip FE of the catheter or it may be arranged behind the catheter at some point of an arteriovenous shunt and, notwithstanding this, fresh blood will still flow around the sensor.

Blood tends to coagulate as soon as its physiological ambient field deviates from sound biological blood vessel surroundings. Hence, the present invention additionally provides the following possibilities of reducing or avoiding a coagulation of blood in the arteriovenous shunt:

The blood has added thereto a small amount of an anticoagulant immediately after entering the arteriovenous shunt.

The arteriovenous shunt consists of the same material, e.g. PVC, with the exception of the arterial and venous catheters.

The arteriovenous shunt or the whole device for controllably maintaining a bloodstream is provided with an antithrombotic internal coating consisting e.g. of heparin. Also the arterial and venous catheters may be provided with such a coating.

The shunt circuit has a constant interior diameter, even at the connecting and branching points, so as to achieve a homogeneous and non-vortical flow within the shunt.

All the ends used for connection with the catheters and the standard Luer-lock connections are provided with special transition pieces, which, when connected to a Luer-lock connection, fill the enlarged interior lumen located in the Luer-lock connection and provide a homogeneous transition which is reduced to the interior diameter of the shunt. Also the transitions to the branching members are homogeneous and constant in cross-section and the branching point within the branching member has an advantageous design from the point of view of fluid mechanics.

The constant interior diameter of the shunt connection is between 0.8 and 1.0 mm, since this diameter corresponds approximately to the interior diameter of the lumen of the catheters and since, in addition, a flow velocity of 10–20 cm per second in the shunt will be obtained when the flow rate is 5–15 ml per minute, said flow velocity corresponding approximately to the normal flow velocity in the radial artery.

Flow rates in the shunt in the order of 5 to 15 milliliters per minute are considered to be sufficient in accordance with the present invention for the purpose of exchanging the blood volume in the surroundings of the sensor in accordance with the typical sensor response time of from 1 to 3 minutes. These flow rates are still very small in comparison with the typical radial arterial flow rates.

There are different possibilities of detecting a situation in which the blood flow rate is low and of informing the operator of this fact by an alarm message in this respect. On the one hand, the behaviour of the blood gas values and of the pH value is characteristic of the flow situation. On the other hand, a temperature sensor, which is normally a constituent part of a blood gas sensor, will provide a display within a very short period of time if a rinsing solution at room temperature reaches this sensor. When a satisfactory amount of blood flows through the catheter, the output-side values of the temperature sensor must be within a range of from two to three degrees below the temperature of the patient's core region. If the temperature is lower than that, this unequivocally indicates that the flow behaviour of the blood in the area of the sensor is insufficient.

The following advantages are achieved by the stepwise approach to the increase in the complexity of the measurement means:

It will suffice to begin with a blood gas monitoring set of minimum complexity which will already be satisfactory for a great number of cases.

The "investment" made for the comparatively expensive disposable blood gas sensors is not lost, since it is not necessary to throw these blood gas sensors away and to replace them by new ones if problems resulting from the flow behaviour arise, the quality of the patient's blood gas monitoring being restorable at comparatively low additional costs, since the additional shunt tubes and connector parts which will then be used are inexpensive disposable parts or throw-away parts and since the pump used can be used again and again in the arrangement in question.

The field of use of continuous blood gas monitoring by means of a sensor which is adapted to be introduced in a vessel can be extended to cases in which only a small amount of blood flows through the vessel in question, this being especially the case with hypothermic patients during open-intracardiac operation or a short time after such operations. These cases have hitherto been those with the highest number of complications when sensors which are adapted to be introduced in the vessel in question have been used in the manner known.

Although the above description of the preferred embodiments concerns blood gas parameter monitoring, it is herewith pointed out that other parameters, such as the electrolyte or glucose values, can also be continuously monitored by small sensors which are adapted to be introduced in the vessel in question. Also this type of sensors must have supplied thereto a flow of fresh blood, independently of the question whether these sensors are introduced in an artery or in a vein. The device according to the present invention can also be used for detecting these parameters so that, upon measuring these parameters, artifacts caused by blood stagnation or blood stasis in the area of the sensor can be excluded.

We claim:

1. A device for continuously detecting blood parameters, comprising:
   a catheter adapted to be introduced, with a free end thereof, into an artery of a patient;
   a sensor arranged on said catheter for detecting blood parameters;
   a tube adapted to be coupled to a vein of the patient and connected to said catheter; and
   a device for controllably maintaining blood flow across said sensor, wherein said device is controlled such that blood flow through the catheter is prevented so as long as the detected blood parameters indicate a sufficient amount of fresh arterial blood flowing around said sensor, and
   if the detected blood parameters indicate that an insufficient amount of blood flows around said sensor, then blood flow through the catheter to the vein of the patient via said tube is established.

2. A device according to claim 1, wherein the device for controllably maintaining a bloodstream from the artery via tube sensor into the vein comprises:
   a first branching member, a first arm of which extends to the catheter, through a second arm of which a sensor cable connected to the sensor extends, and a third arm of which is connected to a rinsing device used for supplying a rinsing solution; and
   a second branching member, a first arm of which extends to said first branching member, through a second arm of which the sensor cable extends to a monitor for blood parameter values, and a third arm of which extends to said tube.

3. A device according to claim 1, wherein
   the catheter, which is adapted to have its free end introduced into an artery of a patient, is a double-lumen catheter comprising two lumina; and
   the sensor is arranged in one lumen of said double-lumen catheter.

4. A device according to claim 3, wherein and a device for supplying a rinsing solution; and
   a sensor cable, which is connected to the sensor, extends through a second lumen of said double-lumen catheter; and
   wherein said device further comprises a branching member comprising a first arm which extends to the second lumen of the double-lumen catheter, a second arm through which the sensor cable extends to a monitor for blood parameter values, and a third arm which serves to drain blood from the artery.

5. A device according to claim 4, further comprising a second branching member, a first arm of which extends to the second arm of the branching member, a second arm of which leads the sensor cable in the direction of the monitor for the blood parameter values, and a third arm of which is connected to the device for supplying the rinsing solution.

6. A device according to claim 4, wherein the first lumen and the interior surface of the second lumen of the double-lumen catheter are coated at least partly with an antithrombotic coating.

7. A device according to claim 4, wherein the first lumen of the double-lumen catheter is coated at least partly with an antithrombotic coating.

8. A device according to claim 4, wherein the interior surface of the second lumen of the double-lumen catheter is coated at least partly with an antithrombotic coating.

9. A device according to claim 3, wherein through one arm of a branching member located next to the catheter a suitable amount of an anticoagulant, is supplied in concentrated form.

10. A device according to claim 3, wherein through one arm of a branching member located next to the arterial catheter a suitable amount of an anticoagulant, is supplied in a suitable solution.

11. A device according to claim 10, wherein the device for controllably maintaining blood flow has a uniform interior diameter between 0.8 and 1.2 mm.

12. A device according to claim 10, wherein the device for controllably maintaining blood flow is produced from one material.

13. A device according to claim 10, wherein the interior surface of the device for controllably maintaining blood flow is coated with an antithrombotic coating.

14. A device according to claim 13, wherein branching members in a shunt are non-releasably connected to hose elements of the shunt.

15. A device according to claim 1, further comprising a pump connected to the device for controllably maintaining a bloodstream and used for pumping blood through the catheter.

16. A device according to claim 15, wherein a first port of the pump is connected to a first arm of a first branching member and a second port of the pump is adapted to be connected to said tube.

17. A device according to claim 15, wherein the pump consists of a hose-roller pump.

18. A device according to claim 15, wherein the pump consists of a manually operated liquid slide valve.

19. A device according to claim 1, wherein parts of the device for controllably maintaining a bloodstream are coated with an antithrombotic coating.

20. A device according claim 1, wherein the device for controllably maintaining a bloodstream has, without including the arterial and any venous catheters, a uniform interior diameter throughout a whole shunt path even across all connecting and branching members, deviations of the diameter of individual connecting and branching members from the uniform interior diameter which do not exceed 30% being still regarded as uniform interior diameter.

21. A device according to claim 1, wherein the device for controllably maintaining blood flow has Luer-lock connection ends and wherein these Luer-lock connection ends are provided with special transition adapters, which, when connected to a Luer-lock connection, will fill an enlarged lumen located in the area of the Luer-lock connection in such a way that, in the connected condition, a homogeneous free interior lumen will be obtained in a connection area of the Luer-lock connection, said interior lumen having a free cross-section which is reduced to the interior diameter of a shunt connection.

22. A device for continuously detecting blood parameters, comprising:
a catheter adapted to be introduced, with a free end thereof, into an artery of a patient;
a sensor arranged on said catheter for detecting blood parameters;
a tube adapted to be coupled to a vein of the patient; and
a device for controllably maintaining a bloodstream from the artery via said sensor and said tube into the vein, said device for controllably maintaining a bloodstream from the artery via said sensor and said tube into the vein comprising:
a first branching member, a first arm of which extends to the catheter, through a second arm of which a sensor cable connected to the sensor extends, and a third arm of which is connected to a rinsing device used for supplying a rinsing solution; and
a second branching member, a first arm of which extends to said first branching member, through a second arm of which the sensor cable extends to a monitor for blood parameter values, and a third arm of which serves to drain blood from the blood vessel.

23. A device for continuously detecting blood parameters, comprising:
a catheter adapted to be introduced, with a free end thereof, into an artery of a patient, wherein the catheter, which is adapted to have its free end introduced into an artery of a patient, is a double-lumen catheter comprising two lumina;
a sensor arranged on said catheter, wherein the sensor is arranged in one lumen of said double-lumen catheter;
a tube adapted to be coupled to a vein of the patient; and
a device for controllably maintaining a bloodstream from the artery via said sensor and said tube into the vein; wherein
a first lumen of said double-lumen catheter is connected to a pressure transducer and a device for supplying a rinsing solution; and
a sensor cable, which is connected to the sensor, extends through a second lumen of said double-lumen catheter; and
said device further comprises a branching member comprising a first arm which extends to the second lumen of the double-lumen catheter, a second arm through which the sensor cable extends to a monitor for blood parameter values, and a third arm which serves to drain blood from the artery.

24. A device for continuously detecting blood parameters, comprising:
a catheter adapted to be introduced with a free end thereof, into an artery of a patient, wherein the first catheter, which is adapted to have its free end introduced into an artery of a patient, is a double-lumen catheter comprising two lumina;
a sensor arranged on said catheter, wherein the sensor is arranged in one lumen of said double-lumen catheter;
a tube adapted to be coupled to a vein of the patient; and
a device for controllably maintaining a bloodstream from the artery via said sensor and said tube into the vein; wherein
a first lumen of said double-lumen catheter is connected to a pressure transducer and a device for supplying a rinsing solution; and
a sensor cable, which is connected to the sensor, extends through a second lumen of said double-lumen catheter; and
said device further comprising;
a branching member comprising a first arm which extends to the second lumen of the double-lumen catheter, a second arm through which the sensor cable extends to a monitor for blood parameter values, and a third arm which serves to drain blood from the artery; and
a second branching member, a first arm of which extends to the second arm of the branching member, a second arm of which leads the sensor cable in the direction of the monitor for the blood parameter values, and a third arm of which is connected to the rinsing device for the rinsing solution.

25. A device for continuously detecting blood parameters, comprising:
a catheter adapted to be introduced, with a free end thereof, into an artery of a patient;
a sensor arranged on said catheter for detecting blood parameters;
a tube adapted to be coupled to a vein of the patient; and a device for controllably maintaining a bloodstream from the artery via said sensor and said tube into the vein;

wherein the device for controllably maintaining a bloodstream has Luer-lock connection ends and wherein these Luer-lock connection ends are provided with special transition adapters, which, when connected to a Luer-lock connection, will fill an enlarged lumen located in an area of the Luer-lock connection in such a way that, in the connected condition, a homogeneous free interior lumen will be obtained in a connection area of the Luer-lock connection, said interior lumen having a free cross-section which is reduced to the interior diameter of a shunt connection.

26. A device for continuously detecting blood parameters, comprising:

- a catheter adapted to be introduced, with a free end thereof, into an artery of a patient;
- a sensor arranged on said catheter for detecting blood parameters;
- a tube adapted to be coupled to a vein of the patient; and
- a device for controllably maintaining a bloodstream from the artery via said sensor and said tube into the vein;

wherein the device for controllably maintaining a bloodstream has, without including the arterial and any venous catheters, a uniform interior diameter throughout a whole shunt path even across all connecting an branching members, deviations of the diameter of individual connecting and branching members from the uniform interior diameter which do not exceed 30% being still regarded as uniform interior diameter;

wherein the interior surface of the device for controllably maintaining a bloodstream is coated with an antithrombotic coating; and wherein branching members in a shunt are non-releasably connected to hose elements of the shunt.

* * * * *

UNITED STATES PATENT AND TRADEMARK OFFICE
CERTIFICATE OF CORRECTION

PATENT NO : 5,687,718
DATED : November 18, 1997
INVENTOR(S) : Fischer et al.

It is certified that error appears in the above-identified patent and that said Letters Patent is hereby corrected as shown below:

In Claim 2 (Column 8, line 14), add "said" after via.

In Claim 2 (Column 8, line 15), delete "sensor" after tube.

In Claim 4 (Column 8, line 33), add "a first lumen of said double-lumen catheter is conneted to a pressure transducer" after wherein.

In Claim 24 (Column 10, line 29), add "," after introduced.

In Claim 24 (Column 10, line 30), delete "first" after the.

Signed and Sealed this

Sixteenth Day of November, 1999

Attest:

Q. TODD DICKINSON

*Attesting Officer*   *Acting Commissioner of Patents and Trademarks*